US010463139B2

(12) United States Patent
Sola et al.

(10) Patent No.: US 10,463,139 B2
(45) Date of Patent: Nov. 5, 2019

(54) HYDRATION SLEEVE AND BLADDER AND RELATED SYSTEMS AND METHODS

(71) Applicant: DGM Creations LLC, West Palm Beach, FL (US)

(72) Inventors: Kyle Sola, Brooklyn, NY (US); Marcel Geser, Zurich (CH); Franziska Rieder, Zurich (CH)

(73) Assignee: DGM Creations LLC, West Palm Beach, FL (US)

( * ) Notice: Subject to any disclaimer, the term of this patent is extended or adjusted under 35 U.S.C. 154(b) by 0 days.

(21) Appl. No.: 15/406,270

(22) Filed: Jan. 13, 2017

(65) Prior Publication Data
US 2017/0202343 A1 Jul. 20, 2017

Related U.S. Application Data

(60) Provisional application No. 62/278,566, filed on Jan. 14, 2016, provisional application No. 62/319,185, (Continued)

(51) Int. Cl.
*A45F 3/20* (2006.01)
*A41D 27/10* (2006.01)
(Continued)

(52) U.S. Cl.
CPC .............. *A45F 3/20* (2013.01); *A41D 27/10* (2013.01); *A61B 5/4875* (2013.01); (Continued)

(58) Field of Classification Search
CPC .................. A45F 3/20; A45F 2003/166; A45F 2005/008; A41D 27/10; B65D 81/3888; (Continued)

(56) References Cited

U.S. PATENT DOCUMENTS 4,736,876 A  4/1988  Kriss
4,974,762 A  12/1990  Boretsky et al.
(Continued)

FOREIGN PATENT DOCUMENTS

EP   2034866        3/2009
GB   2439043 A    12/2007
(Continued)

OTHER PUBLICATIONS

Unpublished Design U.S. Appl. No. 29/568,199, filed Jun. 16, 2016. [Available in IFW].
(Continued)

*Primary Examiner* — Corey N Skurdal
(74) *Attorney, Agent, or Firm* — Venable LLP; Michele V. Frank

(57) ABSTRACT

A hydration sleeve can include: a band of sleeve material shaped and dimensioned to fit around a user's limb; a bladder pocket connected to the band of sleeve material; an opening extending into the bladder pocket to permit insertion of a hydration bladder into the bladder pocket; and a mouthpiece port extending through the band of sleeve material. Other embodiments and features, including single-use hydration bladders and garments incorporating hydration sleeves are described.

12 Claims, 20 Drawing Sheets

Related U.S. Application Data filed on Apr. 6, 2016, provisional application No. 62/383,956, filed on Sep. 6, 2016.

(51) Int. Cl.

| | | |
|---|---|---|
| *A61B 5/00* | (2006.01) | |
| *B65D 81/38* | (2006.01) | |
| *G01F 23/00* | (2006.01) | |
| *G01F 23/02* | (2006.01) | |
| *A45F 3/16* | (2006.01) | |
| *A45F 5/00* | (2006.01) | |

(52) U.S. Cl.
CPC ........ *A61B 5/6804* (2013.01); *B65D 81/3888* (2013.01); *G01F 23/0007* (2013.01); *G01F 23/02* (2013.01); *A41D 2400/46* (2013.01); *A45F 2003/166* (2013.01); *A45F 2005/008* (2013.01)

(58) Field of Classification Search
CPC ... G01F 23/0007; G01F 23/02; A61B 5/4875; A61B 5/6804
See application file for complete search history.

(56) References Cited

U.S. PATENT DOCUMENTS

| | | |
|---|---|---|
| 4,988,097 A | 1/1991 | Smith et al. |
| 5,060,833 A | 10/1991 | Edison et al. |
| D323,430 S | 1/1992 | Niederkorn |
| 5,085,349 A | 2/1992 | Fawcett |
| D327,422 S | 6/1992 | Laing |
| D356,233 S | 3/1995 | Meier |
| D360,805 S | 8/1995 | Friedman |
| D364,536 S | 11/1995 | Law |
| 5,566,869 A | 10/1996 | Katz |
| 5,607,090 A | 3/1997 | Brown |
| 5,727,714 A | 3/1998 | Fawcett |
| 5,794,268 A | 8/1998 | Pessey |
| D398,776 S | 9/1998 | Fawcett |
| 5,803,333 A | 9/1998 | Fawcett |
| 5,806,726 A | 9/1998 | Ho |
| D411,915 S | 7/1999 | George |
| 5,938,089 A | 8/1999 | Abreu-Marston |
| 6,032,831 A | 3/2000 | Gardner et al. |
| 6,070,767 A | 6/2000 | Gardner et al. |
| D435,964 S | 1/2001 | Lentz |
| 6,182,872 B1 | 2/2001 | Six |
| 6,247,619 B1 | 6/2001 | Gill et al. |
| 6,253,379 B1 | 7/2001 | Collier |
| 6,364,168 B1 | 4/2002 | Gardner et al. |
| 6,497,348 B2 | 12/2002 | Forsman et al. |
| 6,626,342 B1 | 9/2003 | Gleason |
| D482,517 S | 11/2003 | Sayers et al. |
| 6,675,998 B2 | 1/2004 | Forsman et al. |
| D490,235 S | 5/2004 | Nykoluk |
| 6,764,064 B2 | 7/2004 | Sturm et al. |
| 6,820,780 B2 | 11/2004 | Forsman et al. |
| 6,892,915 B2 | 5/2005 | Mares |
| 6,908,015 B2 | 6/2005 | Choi et al. |
| 6,990,860 B1 | 1/2006 | Gillanders |
| D517,308 S | 3/2006 | Khalifa |
| 7,014,077 B2 | 3/2006 | Brown |
| 7,063,243 B2 | 6/2006 | Forsman et al. |
| 7,070,075 B2 | 7/2006 | Forsman et al. |
| 7,073,688 B2 | 7/2006 | Choi et al. |
| D538,030 S | 3/2007 | Karl et al. |
| D540,030 S | 4/2007 | Schnackenberg |
| 7,201,299 B2 | 4/2007 | Forsman |
| D547,545 S | 7/2007 | Boehm et al. |
| D560,351 S | 1/2008 | Boehm et al. |
| D570,594 S | 6/2008 | Litvak et al. |
| D577,483 S | 9/2008 | Tagliati et al. |
| 7,478,768 B2 | 1/2009 | Yip |
| D598,643 S | 8/2009 | Lown et al. |
| D611,707 S | 3/2010 | Hock |
| 7,673,777 B2 | 3/2010 | Gleason, Jr. |
| D622,956 S | 9/2010 | Hoffman |
| D637,392 S | 5/2011 | Marshall |
| D640,466 S | 6/2011 | Staton |
| 7,971,549 B2 | 7/2011 | Skillern et al. |
| 8,043,005 B2 | 10/2011 | Lyon et al. |
| D648,934 S | 11/2011 | Ferreiro |
| D655,496 S | 3/2012 | Lamey et al. |
| 8,167,177 B1 | 5/2012 | Galgano |
| 8,177,097 B2 | 5/2012 | Duran |
| 8,186,881 B2 | 5/2012 | Lyon et al. |
| 8,267,283 B2 | 9/2012 | Staton |
| 8,276,785 B1 | 10/2012 | Wheatley et al. |
| 8,341,769 B2 | 1/2013 | Fayle et al. |
| 8,348,114 B2 | 1/2013 | Gleason, Jr. |
| 8,381,956 B2 | 2/2013 | Gleason, Jr. |
| 8,387,831 B2 | 3/2013 | McInerney |
| D680,321 S | 4/2013 | Jones |
| D681,326 S | 5/2013 | Willows et al. |
| D687,222 S | 8/2013 | Willows et al. |
| D690,501 S | 10/2013 | Yetts |
| D691,790 S | 10/2013 | Denzinger |
| 8,561,866 B2 | 10/2013 | Gleason, Jr. |
| 8,579,171 B2 | 11/2013 | Gleason, Jr. |
| 8,622,262 B2 | 1/2014 | Van Art |
| D698,539 S | 2/2014 | Dhillon |
| D701,001 S | 3/2014 | Daniel |
| D708,837 S | 7/2014 | Lee |
| D713,638 S | 9/2014 | Whitlock et al. |
| 8,905,230 B2 | 12/2014 | Smith |
| 8,950,644 B2 | 2/2015 | Gleason, Jr. |
| 9,113,699 B2 | 8/2015 | Radosta |
| 9,238,539 B2 | 1/2016 | Lynch |
| D763,040 S | 8/2016 | Punjabi |
| D778,730 S | 2/2017 | Sahatjian |
| D782,813 S | 4/2017 | Butler |
| 9,615,649 B2 | 4/2017 | Melling et al. |
| 9,624,089 B1 | 4/2017 | Ostrom |
| D785,318 S | 5/2017 | Holmes |
| D787,175 S | 5/2017 | Winters Giesting et al. |
| D802,293 S | 11/2017 | Sola et al. |
| D802,294 S | 11/2017 | Sola et al. |
| D809,285 S | 2/2018 | Sola et al. |
| 10,010,161 B2 * | 7/2018 | Castellanos-Ibanez ..................... A45F 3/20 |
| 2002/0014498 A1 | 2/2002 | Forsman et al. |
| 2002/0056455 A1 | 5/2002 | Vigny et al. |
| 2002/0074369 A1 | 6/2002 | Forsman et al. |
| 2002/0124294 A1 | 9/2002 | McKenzie et al. |
| 2002/0134387 A1 | 9/2002 | Saurat et al. |
| 2002/0179647 A1 | 12/2002 | Hall et al. |
| 2004/0000570 A1 | 1/2004 | Forsman |
| 2004/0089301 A1 | 5/2004 | Choi et al. |
| 2005/0035130 A1 | 2/2005 | Forsman et al. |
| 2006/0151534 A1 | 7/2006 | Mares |
| 2006/0231561 A1 | 10/2006 | Choi et al. |
| 2007/0170216 A1 | 7/2007 | Davis |
| 2007/0280565 A1 | 12/2007 | Lyon et al. |
| 2009/0212081 A1 | 8/2009 | Liang et al. |
| 2009/0293171 A1 | 12/2009 | Fayle et al. |
| 2010/0001022 A1 | 1/2010 | McInerney |
| 2010/0019006 A1 | 1/2010 | Van Art |
| 2010/0059559 A1 | 3/2010 | Given |
| 2010/0213223 A1 | 8/2010 | Ballentine |
| 2012/0048898 A1 | 3/2012 | Franklin et al. |
| 2012/0152986 A1 | 6/2012 | Van Art |
| 2013/0026203 A1 * | 1/2013 | Overton ................. A45C 13/30 224/576 |
| 2013/0026248 A1 | 1/2013 | Paulsen et al. |
| 2013/0056372 A1 | 3/2013 | Lynch |
| 2014/0117058 A1 | 5/2014 | Burtman |
| 2014/0374413 A1 | 12/2014 | Lyon et al. |
| 2014/0376833 A1 | 12/2014 | Lyon et al. |
| 2015/0053718 A1 | 2/2015 | Lyon et al. |
| 2015/0083762 A1 | 3/2015 | Radosta |

(56) References Cited

U.S. PATENT DOCUMENTS

2015/0102058 A1     4/2015   Lyon et al.
2015/0182008 A1     7/2015   Kattouf, II

FOREIGN PATENT DOCUMENTS

WO     2007/144672 A1     12/2007
WO     2015/176124 A1     11/2015

OTHER PUBLICATIONS

Unpublished U.S. Appl. No. 15/638,066, filed Jun. 29, 2017. [Available in IFW].
Notice of Allowance dated Jul. 10, 2017 in Design U.S. Appl. No. 29/575,806.
Notice of Allowance dated Jul. 7, 2017 in Design U.S. Appl. No. 29/551,402.
Notice of Allowance dated Jul. 18, 2017 in Design U.S. Appl. No. 29/575,803.
International Search Report dated Apr. 14, 2017 in International Patent Application No. PCT/US2017/013530.
Written Opinion dated Apr. 14, 2017 in International Patent Application No. PCT/US2017/013530.
Notice of Allowance dated Mar. 13, 2018 in Design U.S. Appl. No. 29/575,804.

\* cited by examiner

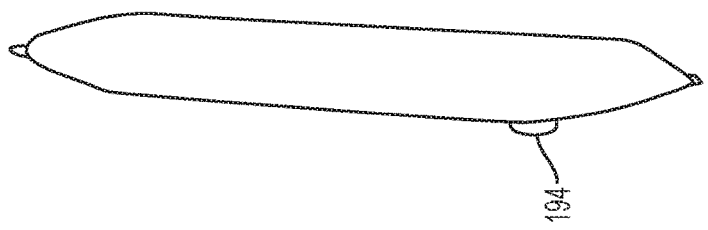
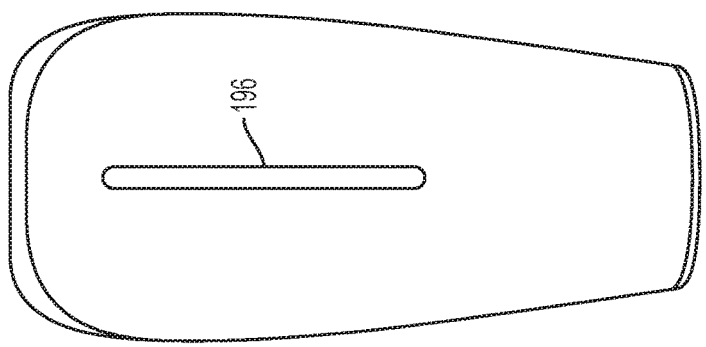
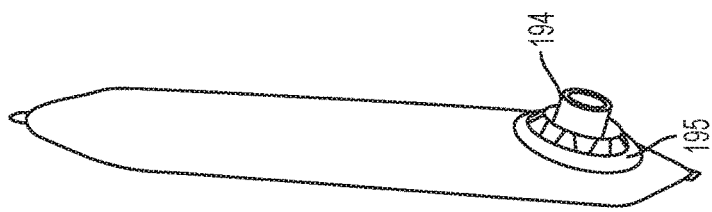
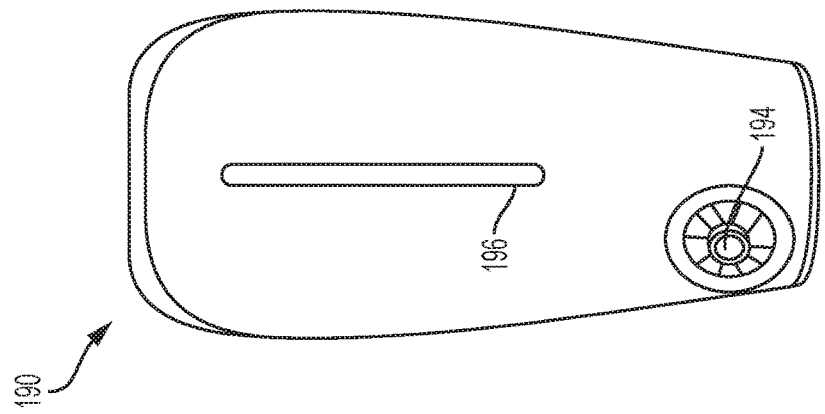

HYDRATION SLEEVE AND BLADDER AND RELATED SYSTEMS AND METHODS

CROSS-REFERENCE TO RELATED APPLICATIONS

This application claims priority under 35 U.S.C. Section 119 to U.S. Provisional Application No. 62/278,566, filed Jan. 14, 2016, U.S. Provisional Application No. 62/319,185, filed Apr. 6, 2016, and U.S. Provisional Application No. 62/383,956, filed Sep. 6, 2016, the entire contents of which are hereby incorporated herein by reference in their entirety. The entire contents of co-owned U.S. Pat. No. 8,387,831 are also incorporated herein by reference.

TECHNICAL FIELD

The present application relates generally to hydration products and related methods. More specifically, the present application relates to a hydration sleeve adapted to be worn on a user's limb, such as the forearm, garments including such a sleeve, hydration bladders, and related methods and accessories.

BACKGROUND

It is often desired to hydrate during activities such as running, cycling, skiing, and surfing, among others. Carrying a water bottle during these types of activities can be inconvenient. Hydration packs are known that can be worn on a person's back, however, hydration packs can be uncomfortable during certain activities such as running. Accordingly, there remains a need for hydration solutions that are convenient, comfortable, and accessible during sporting activities and the like.

SUMMARY OF THE INVENTION

According to an embodiment, a hydration sleeve can include: a band of sleeve material shaped and dimensioned to fit around a user's limb; a bladder pocket connected to the band of sleeve material; an opening extending into the bladder pocket to permit insertion of a hydration bladder into the bladder pocket; and a mouthpiece port extending through the band of sleeve material.

According to an embodiment, a wearable hydration device can include: a sleeve having an interior and an exterior surface; a strap having a first portion and a second portion, the strap being configured to surround at least a portion of the exterior surface of the sleeve; and a bladder pocket that is coupled to the strap, the bladder pocket being configured to receive a hydration bladder.

According to an embodiment, a hydration system can include: a garment having an exterior face; a hydration sleeve integrated into the garment, the hydration sleeve comprising a layer of sleeve material overlaying the garment exterior face and defining a bladder pocket configured to receive a hydration bladder; and a mouthpiece port extending through the layer of sleeve material.

According to an embodiment, a pre-filled, single-use hydration bladder can include: a sealed pouch having an interior chamber pre-filled with a liquid; and a port that is configured to receive a mouthpiece, the port providing fluid communication between the interior chamber and outside of the pouch. The hydration bladder can be shaped to fit inside a bladder pocket that is fixed to a user.

Additional features, advantages, and embodiments of the invention are set forth or apparent from consideration of the following detailed description, drawings and claims. Moreover, it is to be understood that both the foregoing summary of the invention and the following detailed description are examples and intended to provide further explanation without limiting the scope of the invention as claimed.

BRIEF DESCRIPTION OF THE DRAWINGS

The foregoing aspects and other features and advantages of the invention will be apparent from the following drawings, wherein like reference numbers generally indicate identical, functionally similar, and/or structurally similar elements.

FIG. 11A depicts a front-facing view of a hydration bladder, according to an embodiment.

FIG. 11B depicts a right-side view of the hydration bladder of FIG. 11A.

FIG. 11C depicts a rear-facing view of the hydration bladder of FIG. 11A.

FIG. 11D depicts a left-side view of the hydration bladder of FIG. 11A.

DETAILED DESCRIPTION

Embodiments of the invention are discussed in detail below. In describing embodiments, specific terminology is employed for the sake of clarity. However, the invention is not intended to be limited to the specific terminology so selected. A person skilled in the relevant art will recognize that other equivalent parts can be employed and other methods developed without departing from the spirit and scope of the invention.

The present invention relates to a hydration sleeve that can be worn around a user's forearm and used for hydration, for example, during activities such as, but not limited to, running, hiking, cycling, rock climbing, skiing, snowboarding, stand-up paddling, kayaking, fishing, hunting, auto racing, motor sports, and surfing. Additional uses for the hydration sleeve can include military applications, athletic training, triathlons, competitive sports, festivals, theme parks and outdoor recreation. Although the hydration sleeve is described herein as intended for wearing on the user's forearm, it is contemplated that embodiments could alternatively be worn in other areas, such as, for example, around the bicep or calf. According to another aspect, the present invention can relate to garments including integrated hydration systems such as a sleeve for holding a hydration bladder. Hydration bladders, including pre-filled, single-use, disposable bladders, are also described herein.

First Embodiment

Figure 1:
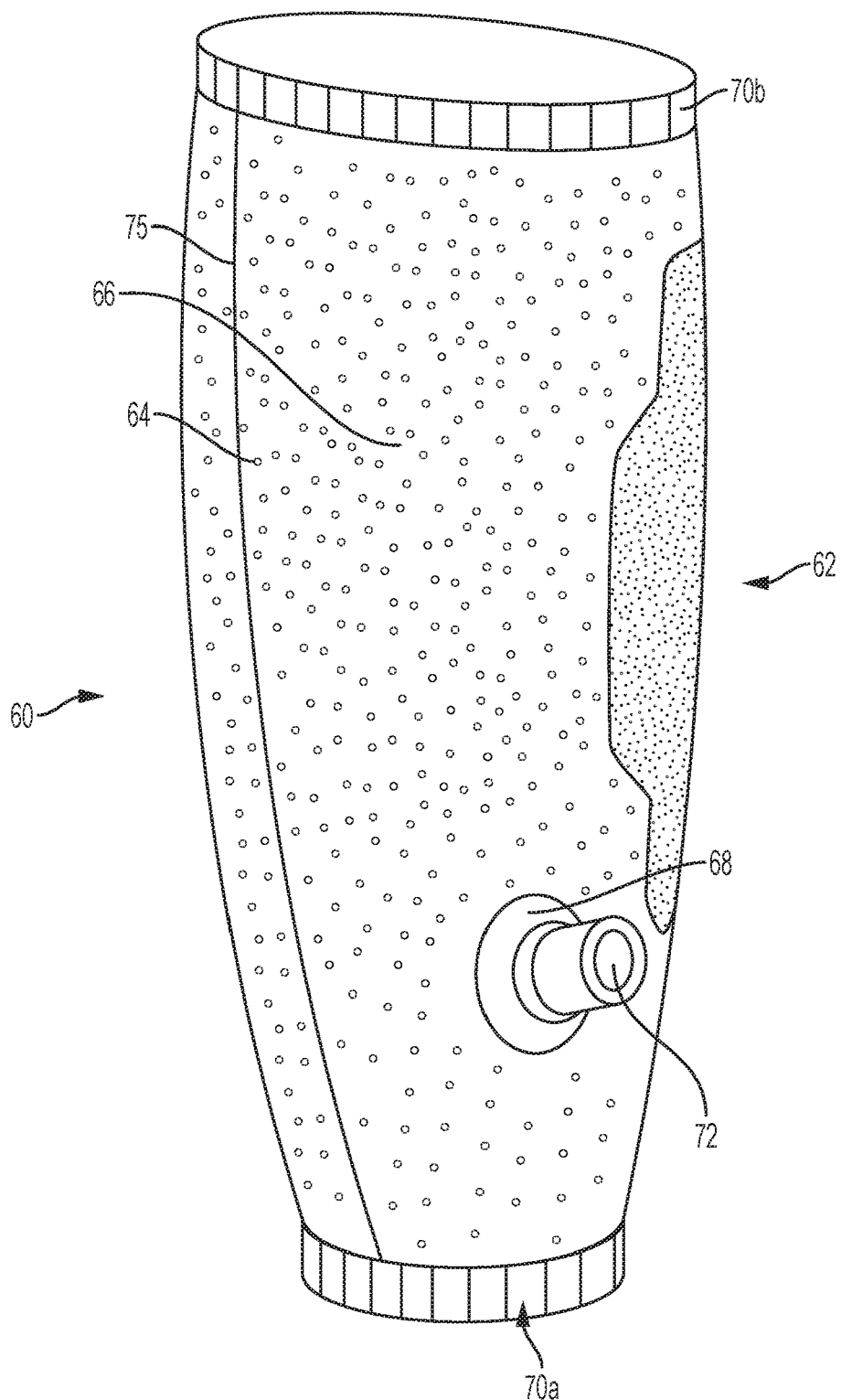
FIG. 1 is a perspective view of an embodiment of a hydration sleeve according to an embodiment.
Figure 2:
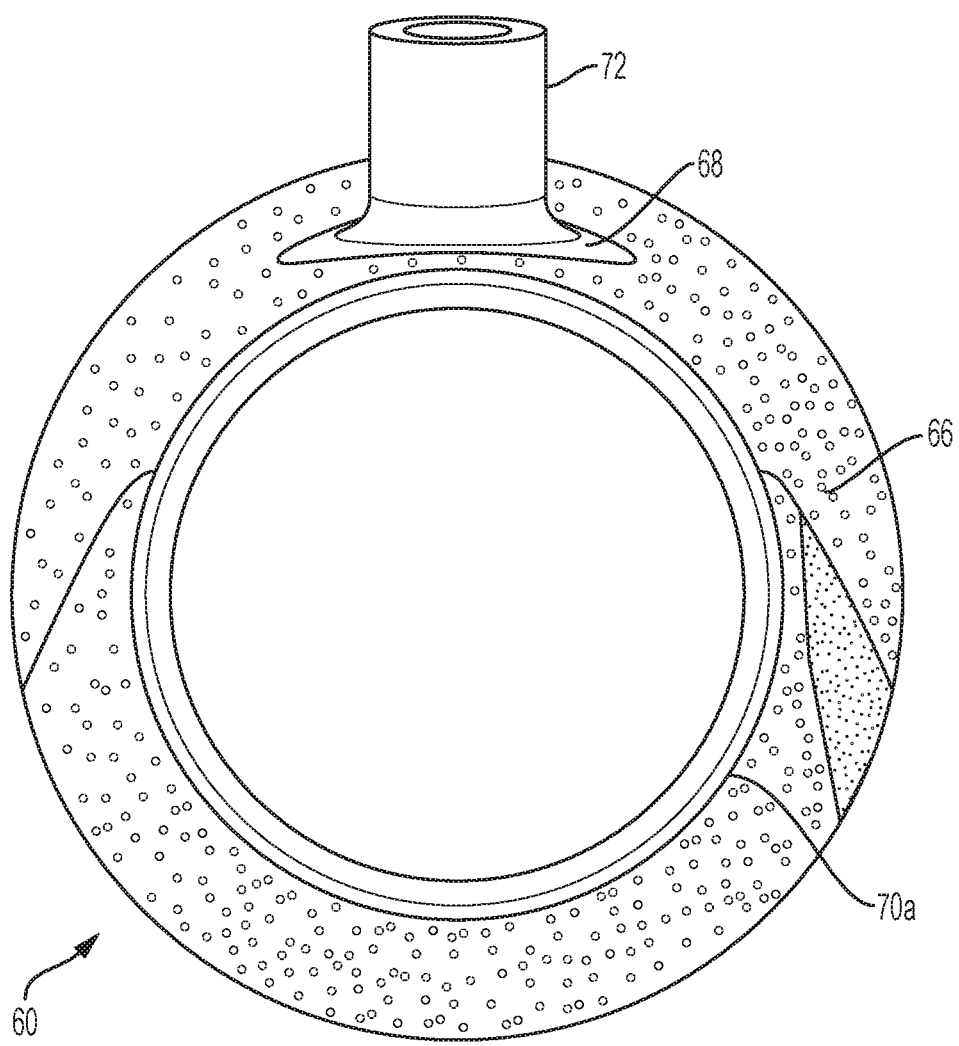
FIG. 2 is an end view of the hydration sleeve of FIG. 1.

FIG. 1 depicts a perspective view of an embodiment of a hydration sleeve 60. FIG. 2 depicts an end view of the hydration sleeve 60 of FIG. 1. The hydration sleeve 60 can generally include an insulated bladder sleeve 66 shaped and dimensioned to fit over a portion of the wearer's limb (e.g., forearm) and a hydration bladder (hidden from view) that fits within the sleeve 66. As shown in FIGS. 1 and 2, the hydration bladder (not shown) or the bladder sleeve 66 itself can include a mouthpiece 72 that extends through a port or other opening in the sleeve 66 to provide the user with access to the mouthpiece 72. According to embodiments, the sleeve 66 can include a sealable opening 62 (see FIG. 1), such as a Velcro™ closure, that permits insertion of the hydration bladder into the sleeve 66. As an alternative to Velcro™, a zipper or other known fastener can be used to close the opening. Still referring to FIGS. 1 and 2, the hydration sleeve 60 can include one or more elastic cuffs 70a, 70b, for example, one located near the user's wrist when worn on the forearm, and another located near the wearer's elbow when worn on the forearm.

According to embodiments, all or a portion of the sleeve 60 can be formed from spandex, polyester, elastic, polyurethane, neoprene, polypropylene, other known "stretchy" fabrics used in athletic gear, and combinations thereof. As depicted in FIG. 1, embodiments of the sleeve can be constructed from multiple panels of material joined together, for example, by stitching, bonding, ultrasonic welding, or other techniques known in the art. Accordingly, the embodiment of FIG. 1 is shown, without limitation, as having a seam 75 running from the proximal elastic cuff 70b to the distal elastic cuff 70a. According to embodiments, one or more segments of the sleeve material can be perforated to enhance breathability. The perforated material can be breathable to keep the hydration sleeve securely in place. As shown in FIG. 1, pores 64 can represent perforations that provide the enhanced breathability of the sleeve material.

According to embodiments, the hydration sleeve 60 can define a length (e.g., from one lateral end to the other lateral end) of between about 7 inches and about 12 inches, however, other lengths may be possible depending on the application and/or intended wearer. The hydration sleeve 60 can define a diameter of between about 3 inches and about 6 inches, however, other diameters may be possible depending on the application and/or intended wearer. In some embodiments, the hydration sleeve 60 can be in a relaxed state having a diameter less than the diameter of between about 3 inches and about 6 inches, but when stretched can be in a stretched state of between about 3 inches and about 6 inches.

In use, the hydration bladder can be filled with an energy gel, water, a sports drink, or another beverage of the user's choosing. The user can wear the sleeve 60 on their forearm during their activity, and can consume the energy gel or beverage through the mouthpiece 72. Any number of mouthpiece designs known in the art can be used to prevent the energy gel or beverage from unintentionally spilling from the bladder. For example, the mouthpiece can be formed from a flexible material such as plastic, silicone, or rubber. The mouthpiece 72 can include a mechanical ("pop-type") closure, a self-healing slit, or any number of other known configurations. Embodiments of the mouthpiece 72 can be removable and replaceable on the bladder to facilitate cleaning and/or replacement with a new mouthpiece.

Figure 3:
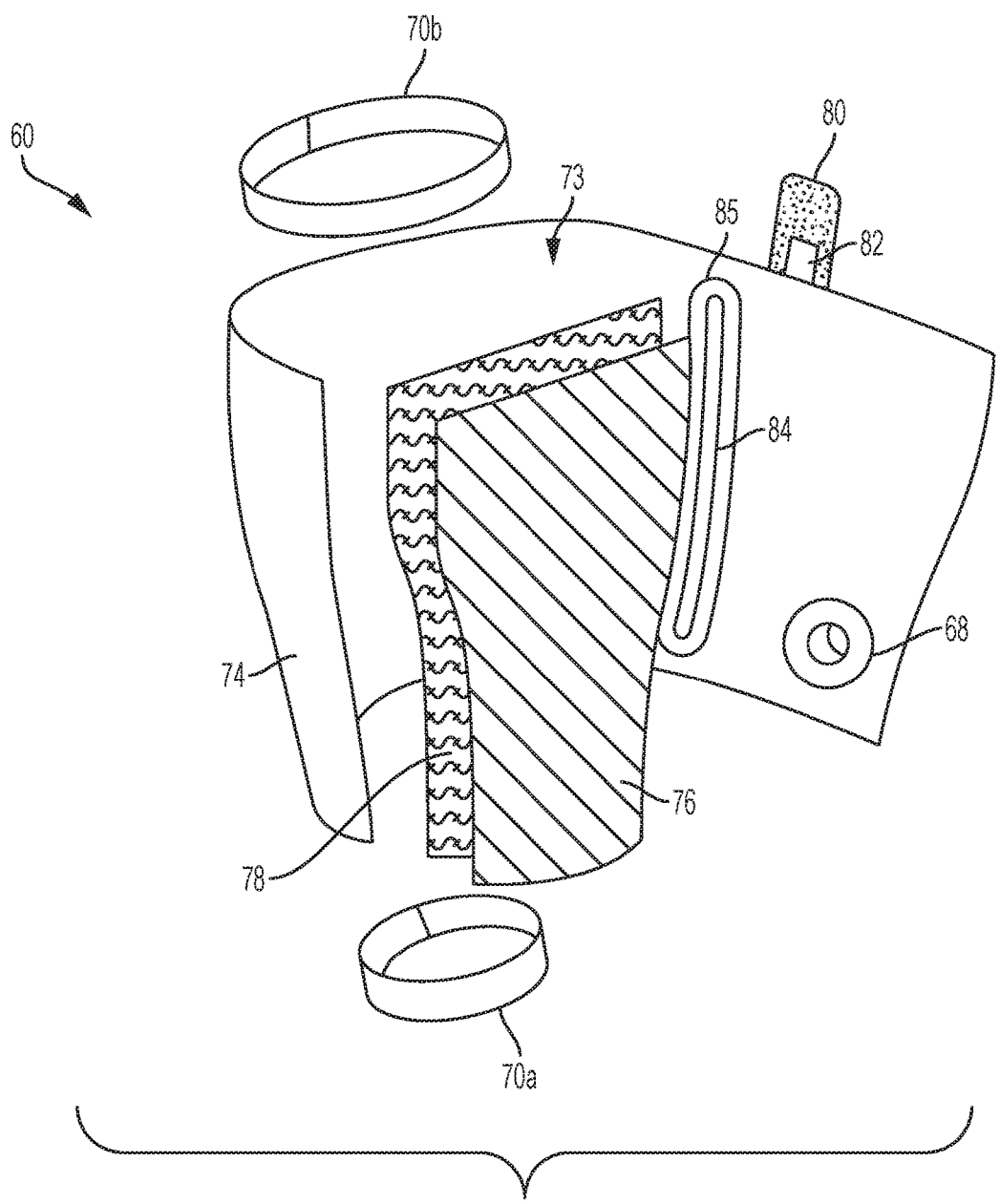
FIG. 3 is an exploded view of the hydration sleeve of FIG. 1, showing an example of how the hydration sleeve can be constructed.

FIG. 3 depicts an exploded view showing an example of how the hydration sleeve 60 may be constructed. According to an embodiment, the sleeve 60 can be formed from a band of sleeve material 74, shown as stretch polyester, having the approximate shape and size of a human forearm. The band can be formed into a substantial tube shape by connecting the opposite ends of the sleeve material 74 together to form a seam (see reference 75 in FIG. 1), for example, by stitching, bonding, ultrasonic welding, or other technique known in the art. Alternative embodiments, including those where the band of sleeve material 74 is monolithic (e.g., formed seamlessly) are also possible. Embodiments may be offered in a variety of sizes to facilitate different sized wearers, or for use during different activities.

The sleeve material 74 can define an elongated pocket opening 84, such as a slit, to facilitate insertion of the hydration bladder. The pocket opening can be bordered by an internal border region 85 (e.g., stitching, edging, overlay, etc.) in order to finish the edges of the opening 84. A similar external border region 80 can also be provided, and can have an opening 82. The sleeve material 74 can also define the mouthpiece port 68, which can comprise a hole or other aperture optionally having its borders finished with stitching, edging, an overlay, a rivet, or other structure known in the art. As discussed above in connection with FIGS. 1 and 2, elastic cuffs 70a, 70b can be located at the opposite ends of the band of sleeve material. The elastic cuffs 70a, 70b can be attached to the sleeve material, for example, by stitching, bonding, ultrasonic welding, or other techniques known in the art. Alternatively, the elastic cuffs 70a, 70b can be formed integrally with the sleeve material. As discussed above, other materials can be used instead of polyester, such as spandex, polyester, elastic, polyurethane, neoprene, polypropylene, other known "stretchy" fabrics used in athletic gear, and combinations thereof. The cuffs 70a, 70b can stretch for a comfortable and secure fit. The elastic cuffs 70a, 70b, if provided, can help to secure the hydration sleeve 60 in place on the wearer's arm. According to embodiments, gripper material can be located on the inner surface of the hydration sleeve to further secure the hydration sleeve in place on the wearer.

Still referring to FIG. 3, the sleeve can define an internal pocket 73 for the hydration bladder, which in the embodiment shown, can be formed by an inner layer of mesh or other breathable lining layer 78 secured to the band of sleeve material 74, however, other embodiments are possible. The breathable lining layer 78 can be disposed between the hydration bladder and the skin of the user for perspiration transport. The material of the breathable lining layer 78 can be comfortable and otherwise be configured to wick moisture away from the user's skin. As an alternative to the breathable lining layer 78, the inner layer can be made from the same or similar material as the sleeve material 74.

The internal pocket 73 can be located between the sleeve material 74 and the inner layer (e.g., breathable lining layer 78). The internal pocket can have dimensions substantially equal to, or slightly larger than, the hydration bladder intended to be used therein. As shown in FIG. 3, a layer of insulating film 76, such as aluminum or other insulating material, can optionally be interposed between the inner layer of the pocket and the sleeve material 74 to help insulate the pocket, and/or to avoid heat transfer between the contents of the bladder and the wearer. The insulating layer 76 can be disposed between the hydration bladder and the skin of the user to reflect body heat away from the contents of the hydration bladder. The inner layer and optional insulating layer 76 can be attached to the sleeve material, for example, by stitching, bonding, ultrasonic welding, or other technique known in the art.

Still referring to FIG. 3, the pocket opening 84 can extend through the sleeve material 74 into the bladder pocket 73. As previously described, a closure can be provided to seal the pocket opening and retain the bladder inside the sleeve. According to the embodiment shown in FIG. 1, a Velcro™ tab 62 can extend along the closure, and the mating Velcro™ material can be located on the sleeve material 66 adjacent to the pocket opening, however, alternative embodiments can use a zipper, snaps, or other structures known in the art. Although not shown, the hydration sleeve of FIG. 3 can house a bladder, for example, of the type shown in FIG. 4 or 5, below, or other suitable hydration bladder known in the art.

Figure 4:
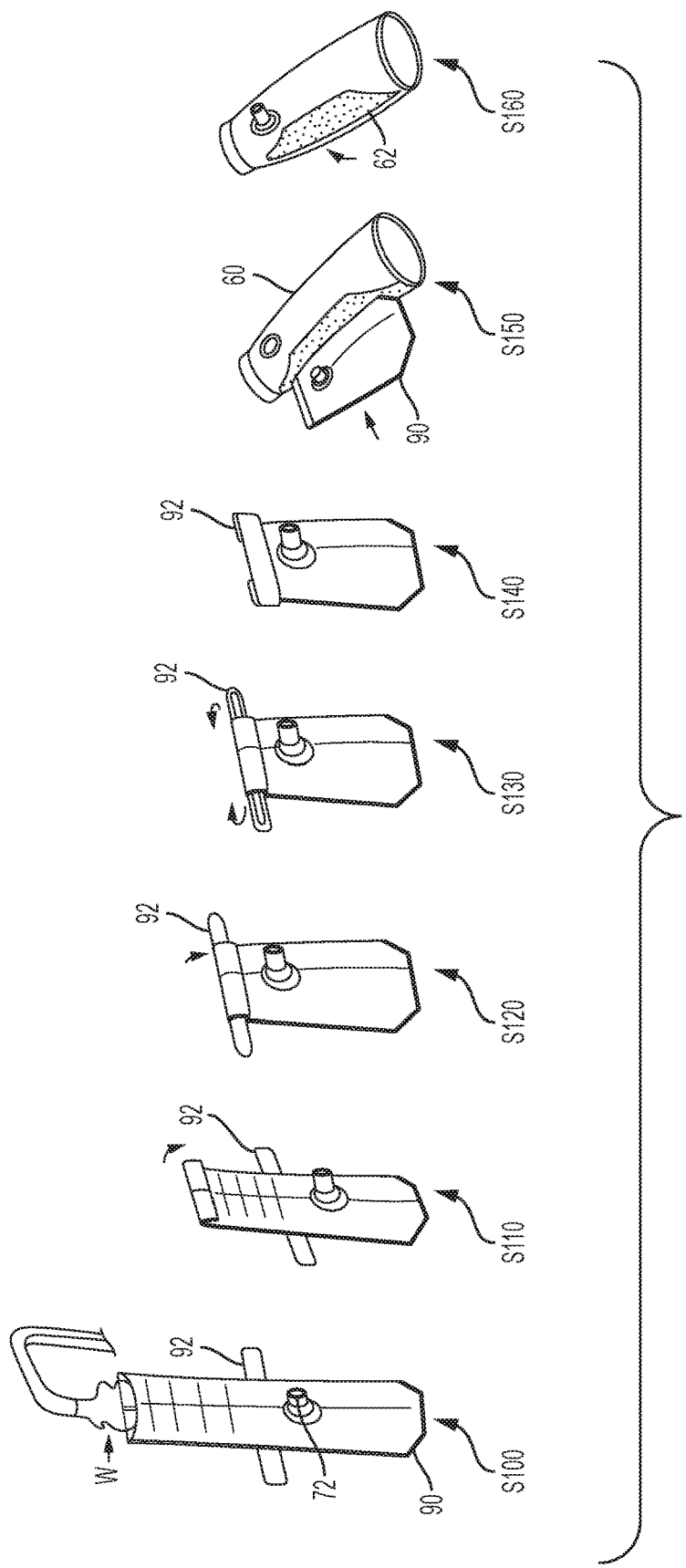
FIG. 4 depicts an exemplary embodiment of a bladder for use in the hydration sleeve, and an example sequence of filling the bladder and inserting it into the bladder pocket of the hydration sleeve of FIG. 3. The depicted bladder construction and sequence of operation are examples only, and are non-limiting.

FIG. 4 depicts an example sequence of using a hydration sleeve. As shown in FIG. 4, step S100 shows that the hydration bladder 90 can include an open "roll" top for filling the bladder with liquids, powders, ice cubes, etc. The bladder 90 can also include a loop of Velcro™ material 92 to seal the open top, as explained in more detail below. One of ordinary skill in the art will appreciate that the hydration sleeve is not limited to the open "roll" top/Velcro™ configuration shown on the bladder in FIG. 4, and that other types of closures, such as a "Zip Lock" type closure can be used to permit filling, emptying, and/or cleaning of the bladder. Alternative embodiments can include a sealed top and incorporate a cap, such as a screw cap, to provide access to the interior of the bladder.

As shown in step S100 of FIG. 4, the bladder 90 can be filled with the user's desired contents (e.g., water W) through the open top. Subsequently, as shown in steps S110 and S120, the user can roll down the excess material at the open top until the volume of the bladder substantially matches the volume of the contents (e.g., when substantially all air is evacuated from the bladder). The Velcro™ material 92 can then be folded back to securely close the top of the bladder, as shown in steps S130 and S140. The rolltop closure mechanism can allow for flexible comfort and easy cleaning. Once the bladder has been filled and sealed, as shown in step S150, the bladder 90 can be inserted into the sleeve 60 through the opening 84 (not shown in FIG. 4) and secured in the pocket using the closure 62, for example, using a Velcro™ closure, to close the sleeve 90 as in step S160. The hydration sleeve 60 can then be placed on the user's limb and used for hydration. The foregoing process can be performed in reverse for emptying, cleaning, and/or refilling the hydration sleeve.

According to embodiments, the hydration bladder 90 can have a capacity of between about 150 mL and about 500 mL, more specifically, between about 200 mL and about 450 mL, for example, about 250 mL, however, other embodiments are possible. According to an embodiment, the hydration bladder can be formed from a flexible, cleanable, non-toxic material, preferably having an anti-microbial treatment. For example, embodiments of the hydration bladder can be formed from polyurethane, polyurethane film, polyester, and other materials known in the art. The bladder material can be FDA approved and can be a BPA free PU film.

Figure 5:
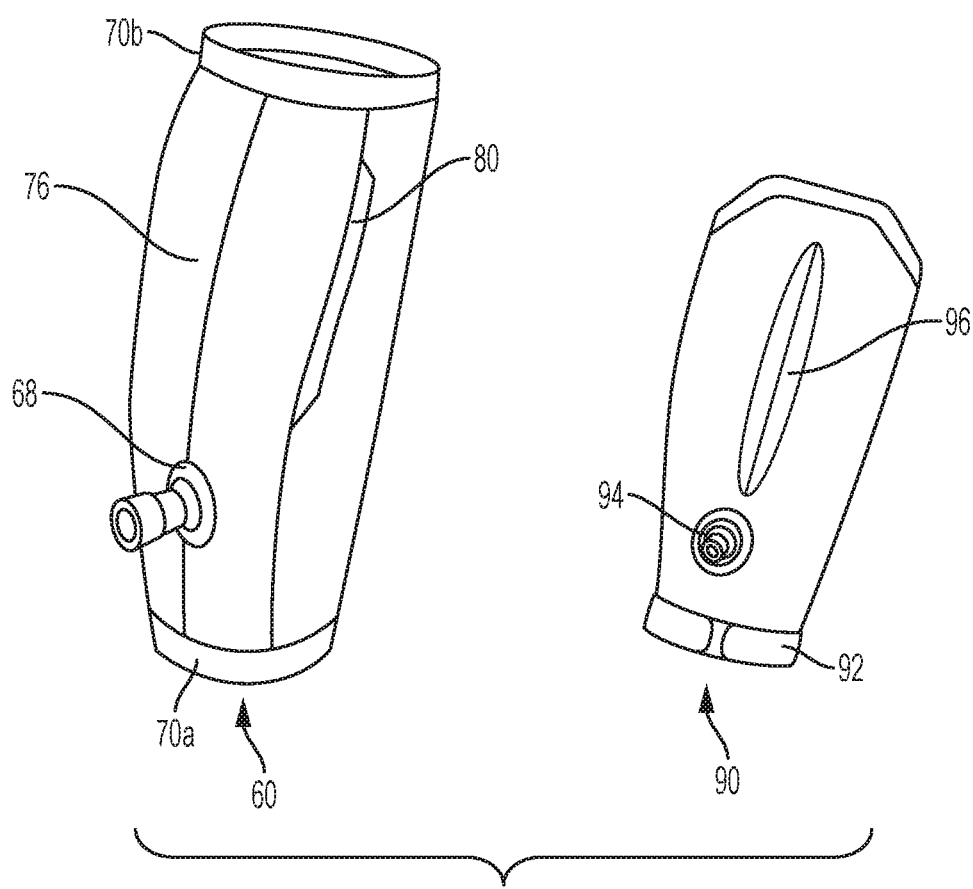
FIG. 5 is a perspective view depicting an embodiment of the hydration sleeve with the bladder removed from the bladder pocket.

FIG. 5 depicts a perspective view of an embodiment of the hydration sleeve 60 with the bladder 90 removed from the bladder pocket. Many of the details shown in FIG. 5 are the same as, or similar to those described herein above. Additional features depicted in FIG. 5 can include an embodiment of an internal "spine" 96 in the bladder 90 to assist the bladder in maintaining the intended shape, and a Hypalon™ tab 80 at the opening of the bladder pocket in order to facilitate easy opening and closing of the bladder pocket. Although not shown, the hydration sleeve 60 can include one or more pockets, for example, with Velcro™ or zipper closure, sized to store items such as keys, money, credit cards, identification, smart devices, energy food, etc. According to embodiments, the one or more pockets can have their opening located on the exterior of the hydration sleeve 60 to facilitate easy insertion and removal of items when wearing the hydration sleeve, although other locations for the opening are possible.

Second Embodiment

Figure 6:
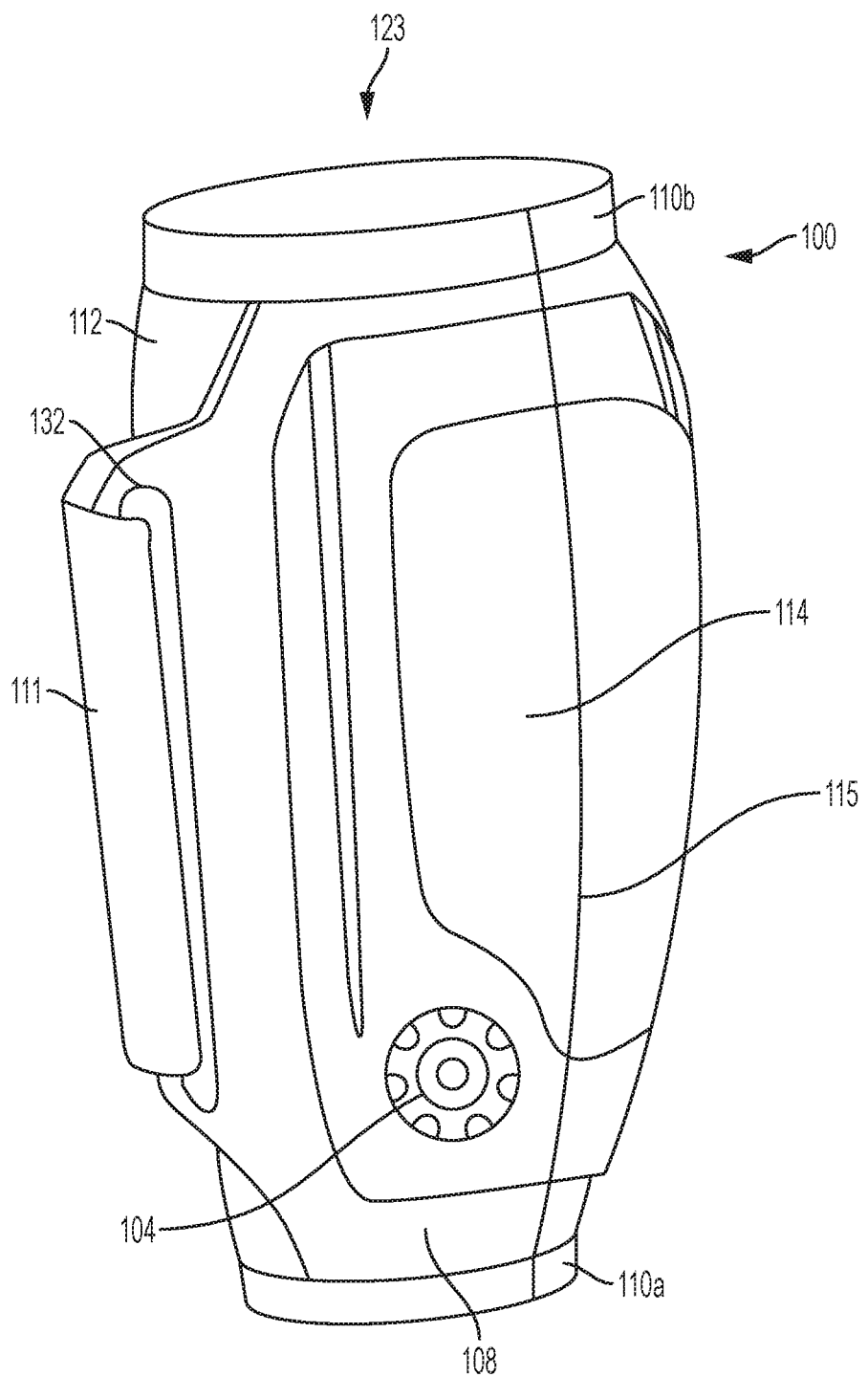
FIG. 6 depicts a perspective view of a hydration sleeve with adjustable strap, according to an embodiment.

Referring to FIG. 6, aspects of the present invention also relate to a hydration sleeve 100 with an adjustable strap 111. Similar to the first embodiment, the hydration sleeve 100 with adjustable strap 111 can generally include a sleeve layer 112 shaped and dimensioned to fit over a portion of the wearer's limb (e.g., forearm) and a hydration bladder (hidden from view) that fits within a bladder pocket 109 (FIG. 7) that overlays the sleeve 112 via an adjustable strap 111. Thus, the hydration sleeve 100 of FIG. 6 can house a bladder, for example, of the types shown in FIGS. 11-14, described below, or other suitable hydration bladder known in the art.

Although not shown, the hydration sleeve 100 with adjustable strap 111 can include one or more pockets, for example, with Velcro™ or zipper closure, sized to store items such as keys, money, credit cards, identification, smart devices, energy food, etc. According to embodiments, the one or more pockets can have their opening located on the exterior of the hydration sleeve 100 to facilitate easy insertion and removal of items when wearing the hydration sleeve, although other locations for the opening are possible.

Figure 7:
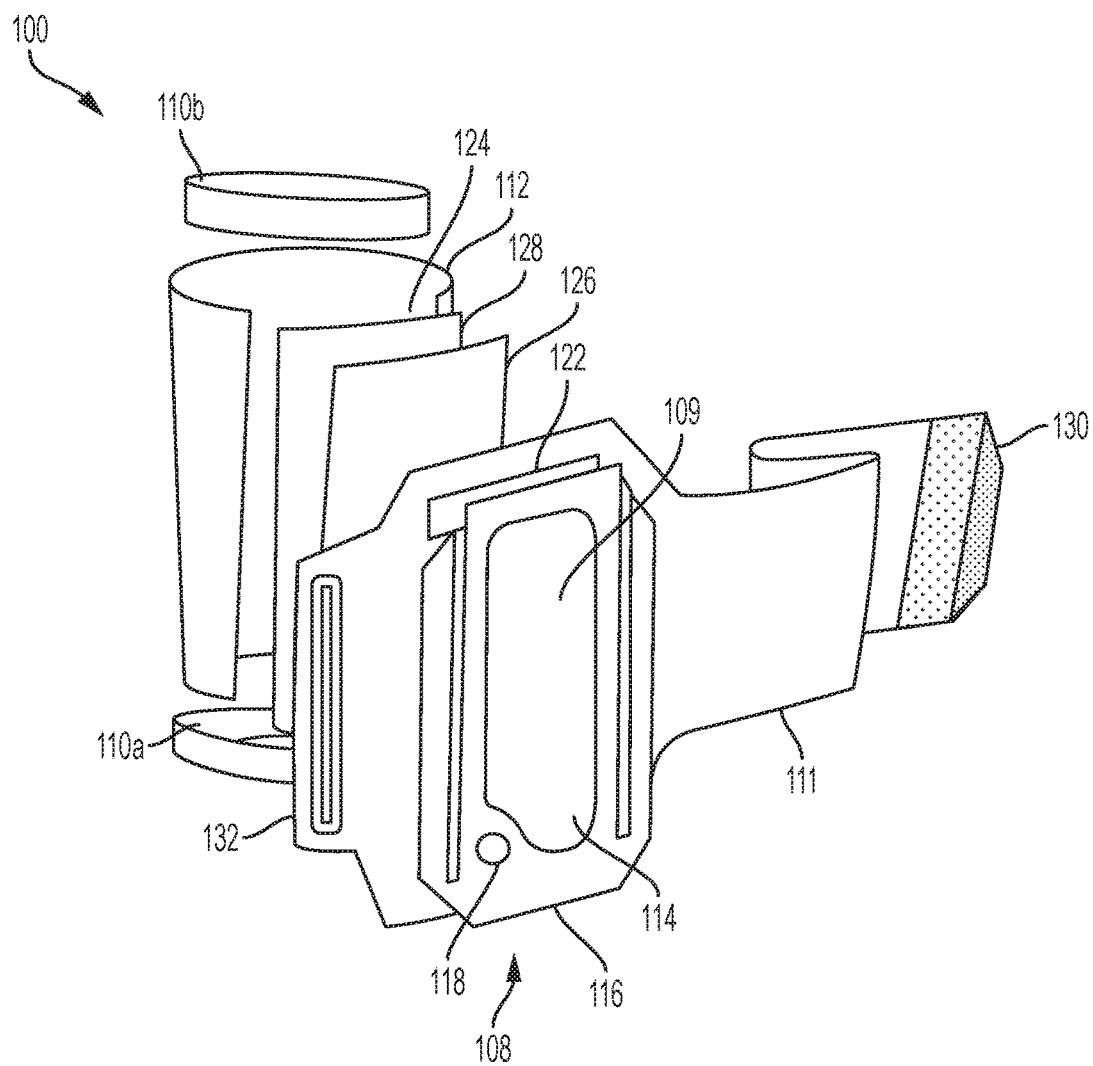
FIG. 7 depicts an exploded, perspective view of a hydration sleeve with adjustable strap, according to an embodiment.

FIG. 7 depicts an exploded view of the hydration sleeve 100, showing an example of how the hydration sleeve 100 may be constructed. Referring to FIGS. 6 and 7 together, according to an embodiment, the sleeve 100 can be formed from a band of sleeve material 112, shown as Lycra™, having the approximate shape and size of a human forearm. Embodiments may be offered in a variety of sizes to facilitate different sized wearers, or for use during different activities. The sleeve can encompass an outer layer 108 (connected to the adjustable strap 111) comprising stretch material that includes hook fastener 130 at one end and a reinforced loop 132 (e.g., plastic reinforced loop) on the other end to facilitate the fastening of the hydration sleeve 100 securely around one's limb.

As shown in FIG. 7, the outer layer 108 can also include a bladder pocket 109 defined by a stretch panel 114 with a non-stretch pocket frame 116 to facilitate insertion of the bladder via an elongated pocket opening 122 with zippers and/or a Velcro™ top closure. The stretch panel 114 can comprise "stretchy" fabrics that allow the user to more easily fit the bladder through the abovementioned pocket opening 122 and into the pocket 109. The pocket opening 122 can be bordered by stitching, edging, an overlay, etc., in order to finish the edges of the opening. The sleeve material can also define the mouthpiece port 118, which can comprise a hole or other aperture optionally having its borders finished with stitching, edging, a rivet, or other structure known in the art. Elastic cuffs 110a, 110b can be located at the opposite ends (distal and proximal) of the band of sleeve material. The elastic cuffs 110a, 110b can be attached to the sleeve material, for example, by stitching, bonding, ultrasonic welding, or other techniques known in the art. Alternatively, the elastic cuffs 110a, 110b can be formed integrally with the sleeve material. Other materials can be used instead of Lycra™, such as spandex, polyester, elastic, polyurethane, Elastane, neoprene, polypropylene, other known "stretchy" fabrics used in athletic gear, and combinations thereof. According to embodiments, one or more segments of the sleeve material 74 can be perforated to enhance breathability.

As depicted in FIG. 7, embodiments of the sleeve can be constructed from multiple panels of material joined together, for example, by stitching, bonding, ultrasonic welding, or other techniques known in the art. Accordingly, the embodiment of FIG. 6 is shown, without limitation, as having a seam 115 running from the proximal elastic cuff 110b to the distal elastic cuff 110a. It is also understood that the embodiments of the sleeve, as depicted in FIG. 7, do not have to be joined together and can be used separately. For example, as discussed further herein below, a wearer may opt to use the outer layer 108 that includes an adjustable strap 111, bladder pocket 109, and pocket frame 116 to insert the bladder by itself without use of the underlying sleeve material 112. In other words, the adjustable strap 111, bladder pocket 109, and pocket frame 116, which holds the hydration bladder, can be connected (e.g., sewn) to the sleeve material 112 in some embodiments, and can be disconnected from the sleeve material 112 in other embodiments.

As with the first embodiment, the hydration sleeve 100 can define a length (e.g., from one lateral end to the other lateral end) of between about 7 inches and about 12 inches; however, other lengths may be possible depending on the application and/or intended wearer. The hydration sleeve can define a diameter of between about 3 inches and about 6 inches, however, other diameters may be possible depending on the application and/or intended wearer. In some embodiments, the hydration sleeve can be in a relaxed state having a diameter less than the diameter of between about 3 inches and about 6 inches, but when stretched can be in a stretched state of between about 3 inches and about 6 inches.

The elastic cuffs 110a, 110b, if provided, can help to secure the hydration sleeve 100 in place on the wearer's arm. According to embodiments, gripper material can be located on the inner surface 124 of the hydration sleeve 100 to further secure the hydration sleeve in place on the wearer.

Still referring to FIG. 7, the sleeve 100 can also include an inner layer, such as a mesh layer 128, secured to the sleeve material 112. The layer of mesh 128 can be a 3D mesh. As an alternative to the mesh material, the inner layer can be made from the same or similar material as the sleeve material. The non-stretch bladder pocket frame 116 can have dimensions substantially equal to, or slightly larger than, the bladder intended to be used therein. The non-stretch bladder pocket frame 116 houses the bladder and the non-stretch nature of the fabrics used therein can ensure that the bladder does not move around freely once inserted through the pocket opening 122. As shown in FIG. 7, a layer of insulating material 126, such as aluminum or other insulating material, can optionally be used to help insulate the bladder, and/or to avoid heat transfer between the contents of the bladder and the wearer. The layer of mesh 128 and optional insulating layer 126 can be attached to the sleeve material, for example, by stitching, bonding, ultrasonic welding, or other technique known in the art.

Figure 9:
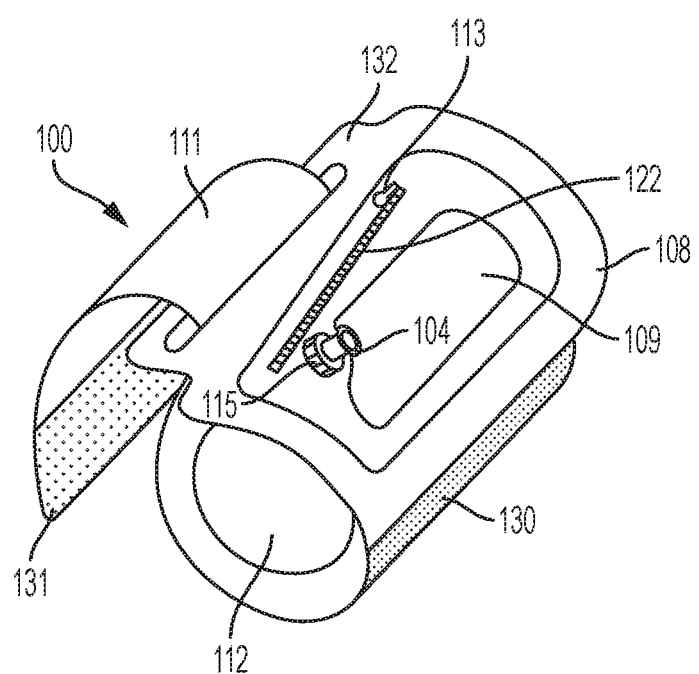
FIG. 9 is an end-perspective view of a hydration sleeve with a detached, adjustable strap, according to an embodiment.

According to embodiments shown in FIGS. 7 and 9, the sleeve 112 can be a Lycra™ sleeve and can include a sealable opening, such as a Velcro™ closure. A strap 111 can thus include a hook fastener 130 and a loop fastener 131, which can include Velcro™ to secure the bladder pocket. Thus, the sleeve can permit insertion of the bladder into a stretch panel or outer shell with bladder pocket. As an alternative, or in addition to Velcro™, a zipper or other known fastener can be used to close the opening. The strap 111 can allow the user to securely fasten the sleeve against the user's limb via the hook fastener 130 and loop fastener 131 once inserted through the plastic reinforced loop 132. In an embodiment, the strap 111 can be a stretch closure wrap. As an alternative to the abovementioned construction, the outer layer 108 need not be affixed to the Lycra™ sleeve underneath it. To that end, the user may alternatively wear the outer layer 108 and all its abovementioned features, including the stretch closure wrap and loop fastener directly on top of the user's limb (or article of clothing) without using the Lycra™ sleeve component.

Figure 8:
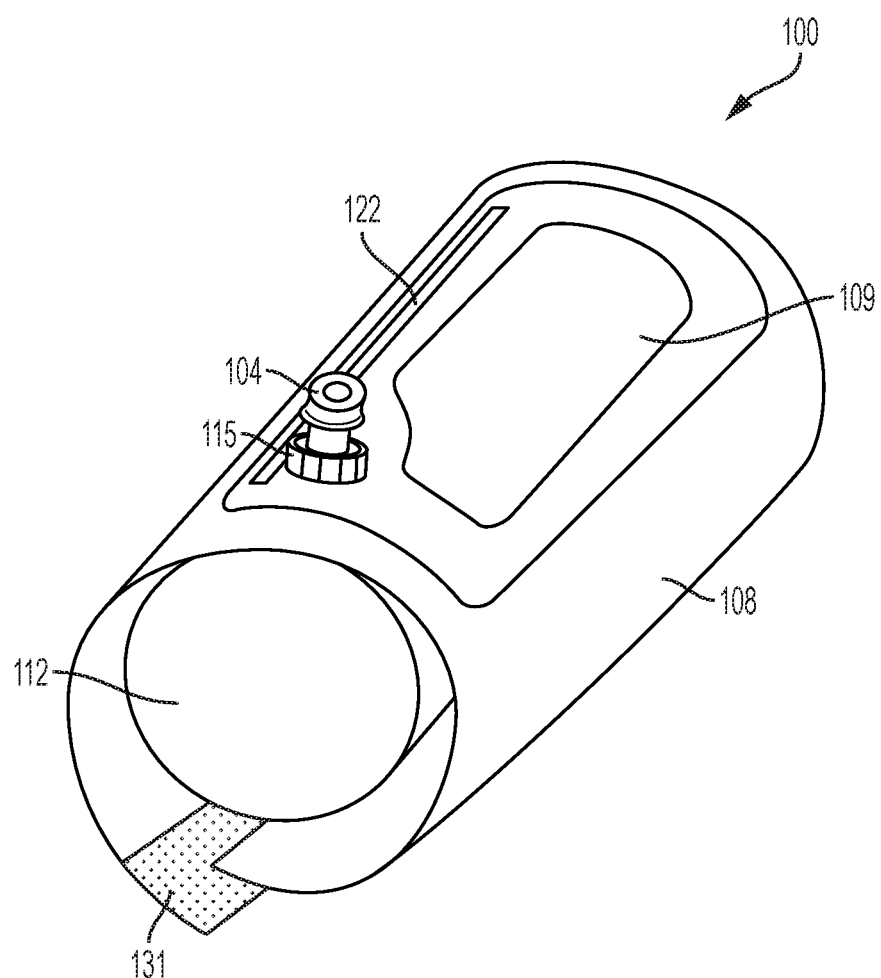
FIG. 8 is an end-perspective view of a hydration sleeve with adjustable strap, according to an embodiment.

FIG. 8 depicts an exploded view of certain elements of the hydration sleeve 100, including, but not limited to, the sleeve material 112 surrounded by the outer layer 108 that encompasses the adjustable strap 111, bladder pocket 109 having the pocket opening 122, as well as the loop fastener 131. A mouthpiece 104 and port 115 are also shown, among other features. FIG. 9 depicts a variation where the bladder pocket opening 122 includes a zip closure 113 to secure the bladder (not shown) in the bladder pocket 109.

Figure 10D:
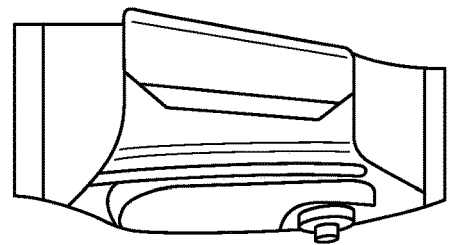
FIG. 10D depicts a left-side view of the hydration sleeve of FIG. 10A.
Figure 10C:
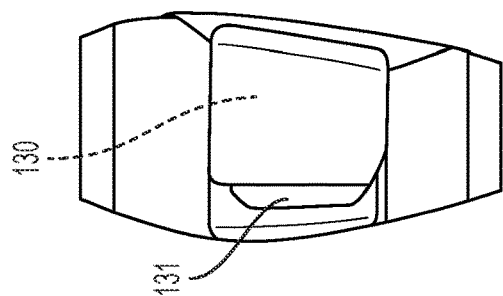
FIG. 10C depicts a rear-facing view of the hydration sleeve of FIG. 10A.
Figure 10B:
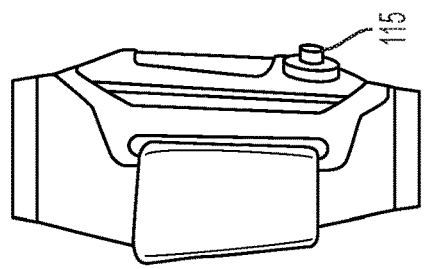
FIG. 10B depicts a right-side view of the hydration sleeve of FIG. 10A.
Figure 10A:
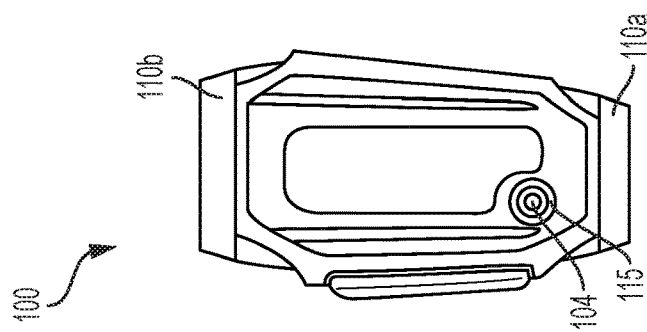
FIG. 10A depicts a front-facing view of a hydration sleeve with adjustable strap, according to an embodiment.

FIGS. 10A-10D depict multiple side views of the hydration sleeve 100. FIG. 10A shows a front view of the hydration sleeve with the hydration bladder's mouthpiece 104 extending through port 115. FIG. 10B shows a right side view. FIG. 10C shows a rear view of FIG. 10A, showing the loop fastener 131 attached to a hook fastener 130. FIG. 10D shows a left side view of FIG. 10A.

Other Features

Embodiments of the hydration sleeve can incorporate sensor technology (such as, e.g., one or more chips or hydration sensors located in or on the hydration sleeve, or "smart fabrics") to provide the wearer with information on various physiological states and levels. For example, an embodiment can have a hydration sensor that monitors the wearer's hydration levels, and provides feedback regarding same, such as an indication of when to drink from the hydration sleeve. According to an embodiment, the sleeve can have an integrated, non-invasive flat strip wraparound sensor underneath the base layer that touches the skin of the forearm, however, other locations and placements of the sensor are possible. The sensor can measure the user's hydration levels and inform the user via either a small screen (situated on top of the sleeve), a color coding scheme (also via the top layer of the sleeve), sounds, vibrations, or combinations thereof indicating that he/she should drink more from the sleeve in order to achieve optimal hydration levels. Other sensor and feedback schemes are also contemplated.

Additionally, or alternatively, the sensor technology can be used to indicate the amount of liquid left in the bladder and can aggregate consumption data. According to embodiments, the sensor could identify the percentage of the bladder that is full, or alternatively, could simply alert the wearer when the contents of the bladder fall below a certain level. An electronic display located on the hydration sleeve could be used to indicate the contents level (and additionally, the wearer's hydration level as discussed above). According to alternative options, a window through the sleeve itself could be used to provide the wearer with a visual indication of the amount of liquid left in the bladder. These types of hydration feedback sensors can be provided with or without the adjustable strap.

Bladders

FIGS. 11-14 depict various embodiments of a bladder 190. As one of ordinary skill in the art will appreciate, the bladder 190 can either be refilled and reinserted into the hydration sleeve after each use, or can be a pre-filled bladder that is intended to be disposed of upon consuming its liquid contents. One of ordinary skill in the art will also appreciate that refillable embodiments of the hydration sleeve are not limited to a specific closure and that various types of closures, such as a "Zip Lock" type closure, or open "roll" top Velcro™ can be used to permit filling, emptying, and/or cleaning of the bladder. Alternative embodiments can include a sealed top and incorporate a cap, such as a screw cap, to provide access to the interior of the bladder 190. Embodiments can include pre-filled, single-serve bladders. Embodiments of this type of bladder can come with or without a mouthpiece installed.

FIGS. 11A-11D show a bladder 190 according to embodiments of the invention. FIG. 11A shows a front view of the bladder 190. As shown in FIG. 11A, embodiments of the bladder 190 can include a mouthpiece 194 through which the user can drink the contents of the bladder 190. The bladder 190 can include a spine 196 located insider the bladder 190 that provides support and also maintains a separation between the layers of the bladder 190. According to an alternative embodiment, the spine 196 can be located externally to the bladder. FIG. 11B shows the right side of bladder 190. FIG. 11C shows the rear of bladder 190. The spine 196 can be disposed on a single side of the bladder 190, or multiple spines 196 can be located on multiple sides of the bladder. For example, the spine 196 can be disposed on a front side as shown in FIG. 11A and/or disposed on a rear side, as shown in FIG. 11C. FIG. 11D shows a left side of the bladder 190.

Figure 12:
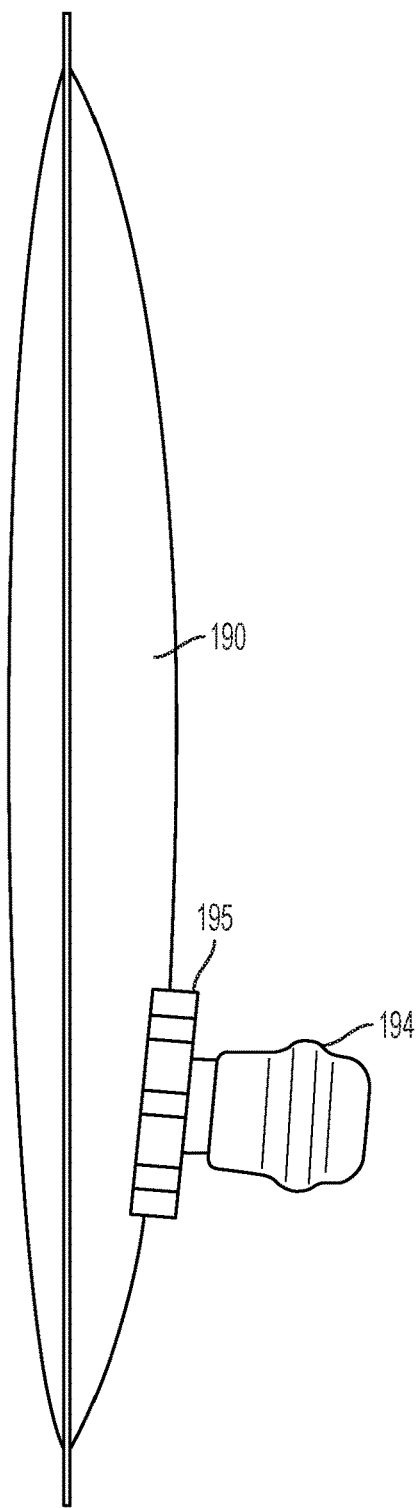
FIG. 12 depicts a side view of a hydration bladder, according to an embodiment.

In use, the bladder can be filled with an energy gel, water, a sports drink, or another beverage of the user's choosing. The user can wear the bladder on their forearm during their activity, and can consume the energy gel or beverage through the mouthpiece 194. With reference to FIG. 12, the mouthpiece 194 can either be affixed to the bladder or serve as an accessory that connects to a fitment seal 195 on the face of the bladder 190. The fitment seal 195 can be a low-profile fitment containing a seal that enables a connection between the bladder 190 and the mouthpiece 194, for example, using a threaded or cam-lock feature.

Any number of mouthpiece designs known in the art can be used to prevent the energy gel or beverage from unintentionally spilling from the bladder. For example, the mouthpiece can be formed from a flexible material such as plastic, silicone, or rubber, and can also include a screw cap closure attached to the mouthpiece. The mouthpiece can include a mechanical ("pop-type") closure (FIG. 12), a self-healing slit (FIGS. 11 and 13), or any number of other known configurations. Embodiments of the mouthpiece and screw cap can be removable and replaceable on the bladder to facilitate cleaning and/or replacement with a new mouthpiece.

The bladder can be filled with the user's desired contents through the opening. Once the bladder has been filled and sealed, it can be inserted into the bladder pocket. The hydration sleeve can then be placed on the user's limb and used for hydration. The foregoing process can be performed in reverse for emptying, cleaning and/or refilling the hydration sleeve. One of ordinary skill in the art will also appreciate that a pre-filled, single use, disposable bladder may be pre-filled with liquid and sealed shut so that the user does not have to empty, clean, and/or refill the bladder in order to refill the hydration sleeve. Rather, the pre-filled, disposable bladder can come pre-filled and factory sealed, intended for a single usage. To avoid wasting the mouth piece, which can be expensive to manufacture, pre-filled, disposable bladders can come with a threaded, cam-lock, or other port that is adapted to connect to a re-useable mouth piece; in which case, the bladder can be factory sealed prior to usage.

According to embodiments, the bladder can have a capacity of between about 150 mL and about 500 mL, more specifically, between about 200 mL and about 450 mL, for example, about 250 mL, however, other embodiments are possible. According to an embodiment, the refillable bladder can be formed from a flexible, cleanable, non-toxic material, preferably having an anti-microbial treatment. For example, embodiments of the refillable bladder can be formed from polyurethane, polyurethane film, polyester, and other materials known in the art. Alternatively, embodiments of the disposable bladder can be formed from polypropylene or Polyethylene terephthalate, and other materials known in the art.

Figure 13:
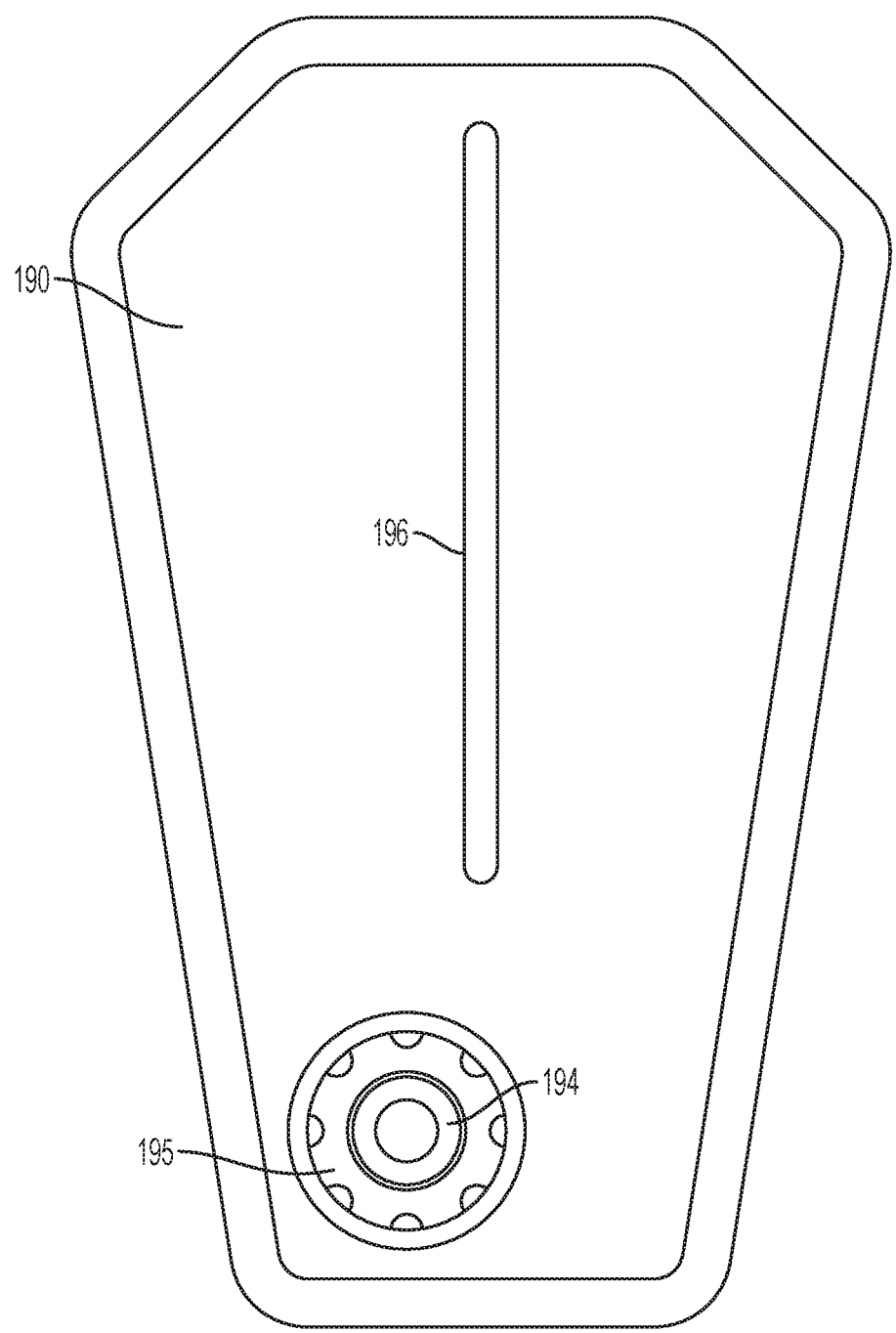
FIG. 13 is a front-facing view of the hydration bladder of FIG. 12.
Figure 14:
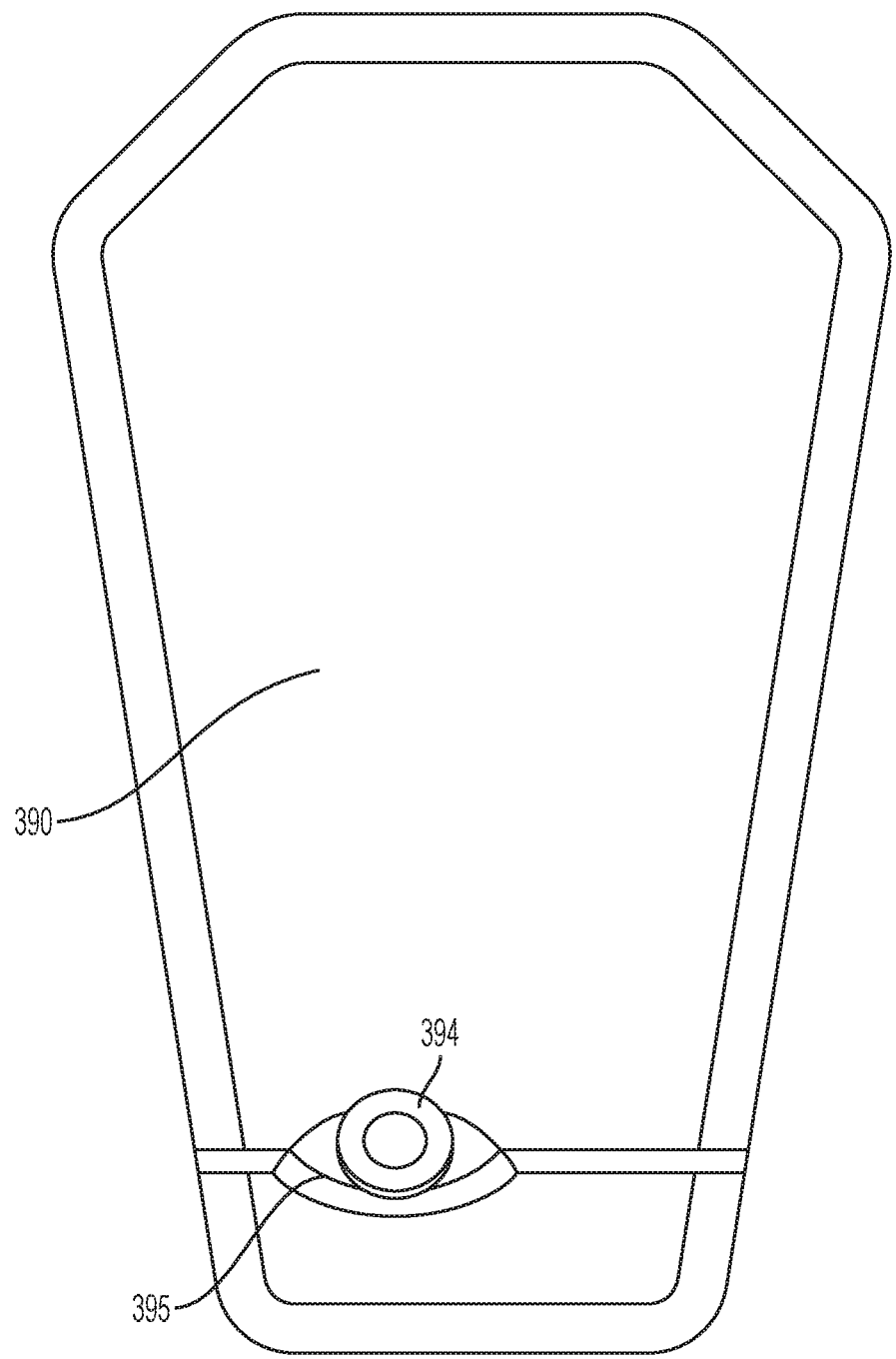
FIG. 14 is a front-facing view of a hydration bladder, according to an embodiment.

FIG. 13 depicts an embodiment of a bladder 190 having a relatively rigid, internal spine 196 (e.g., formed of plastic) on one side of the bladder to assist the bladder in maintaining the intended shape. Thus, the spine 196 can maintain a 3-D shape of the bladder. As discussed above, the spine 196 can be located inside the bladder 190, or can be located externally. Additionally, embodiments can include one or more spines 196 in various locations. FIG. 14 depicts an embodiment of a bladder 390 having a mechanical ("pop-type") closure.

Garment Integration

Figure 15:
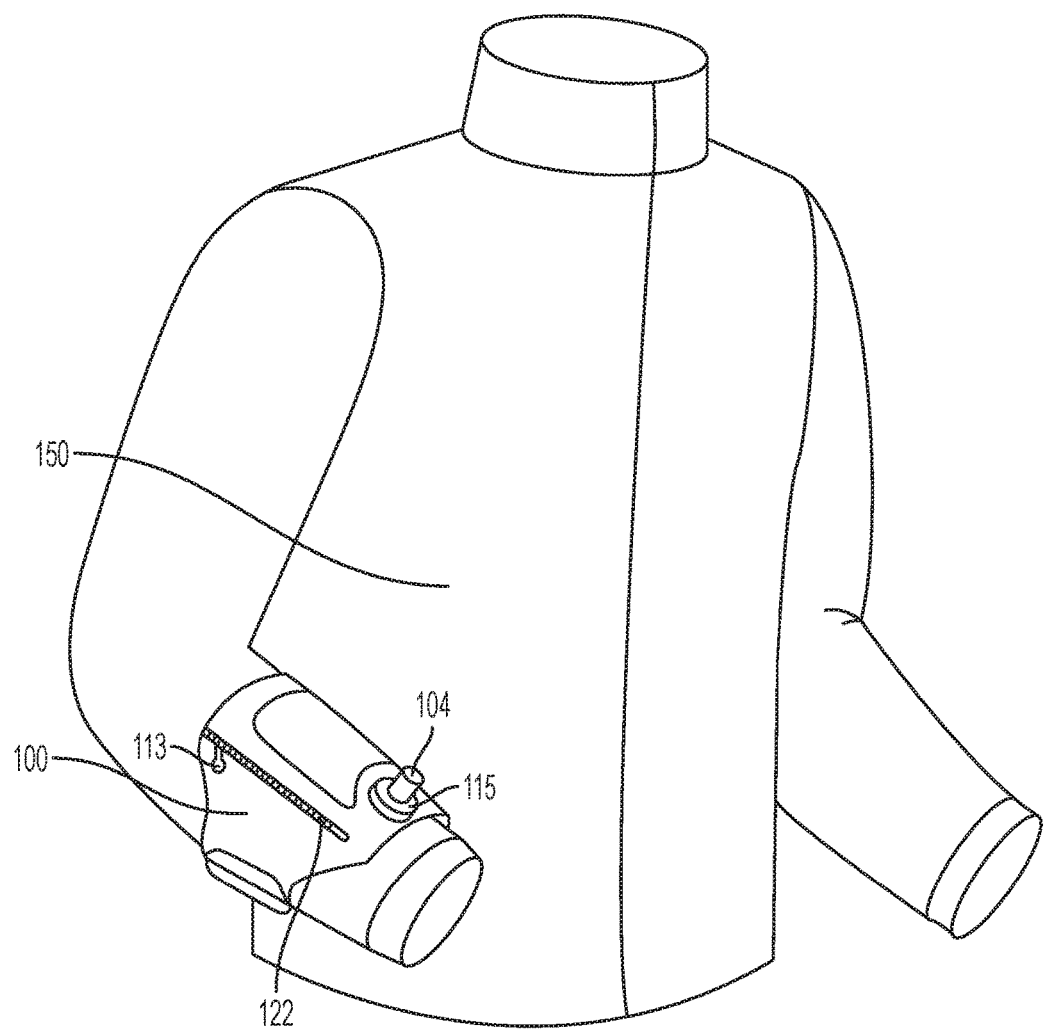
FIG. 15 shows a perspective view of a garment having a hydration sleeve, according to an embodiment.
Figure 16:
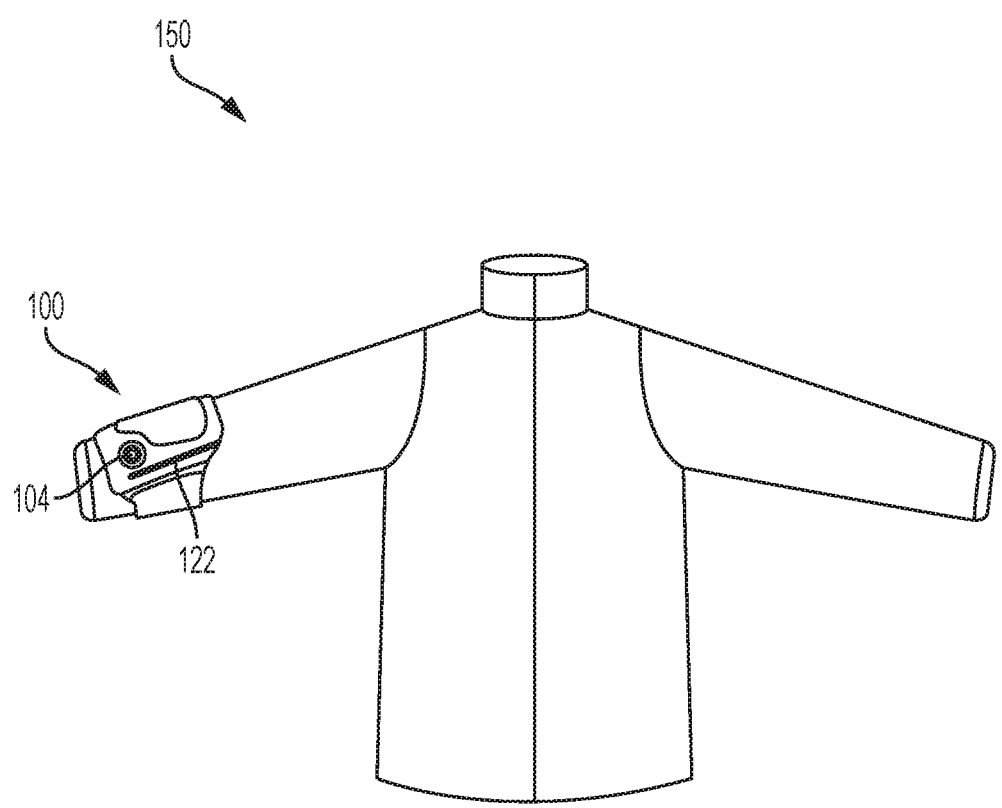
FIG. 16 is a front-facing view of the garment of FIG. 15.
Figure 17:
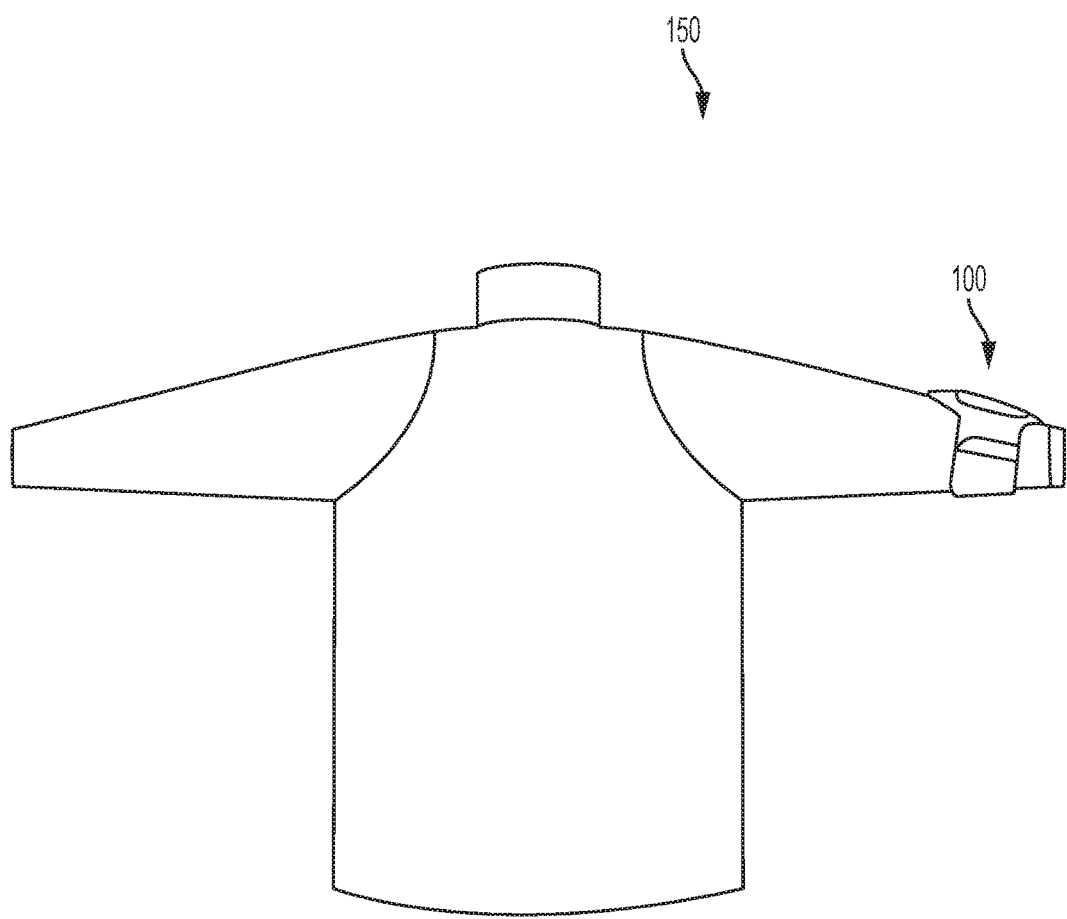
FIG. 17 is a rear-facing view of the garment of FIG. 15.

FIGS. 15-17 depict embodiments of a hydration sleeve being worn on top of, or integrated into, the forearm of an outerwear garment 150. Specifically, FIGS. 15-17 show the embodiments of hydration sleeve 100 of FIGS. 6-8 worn over the exterior surface of a sleeve of the outerwear garment 150. The hydration sleeve 100 can be wrapped around an exterior surface of the garment's sleeve and can be secured thereto, for example, using the attachment strap 111. In this case, the hydration sleeve may be used without the sleeve 112, and the adjustment strap 111 can be used to secure the bladder pocket 109 over the garment's sleeve. The zip closure 113 can be used to secure the bladder (not shown) in the bladder pocket 109. The bladder pocket 109 can be opened and closed by means of the zipper. According to alternative embodiments, the hydration sleeve 100 can include the sleeve layer 112, which can be worn on top of the garment's sleeve.

According to embodiments, the hydration sleeve 100 can have at least a portion, for example an interior surface area, that is attached to or part of the sleeve of the outerwear. Even though FIG. 15 shows the hydration sleeve 100 disposed on a distal portion of the sleeve of the outerwear garment 150, the hydration sleeve 100 can be disposed around more proximal positions of the garment sleeve or in other portions of the outerwear garment 150.

Figure 18:
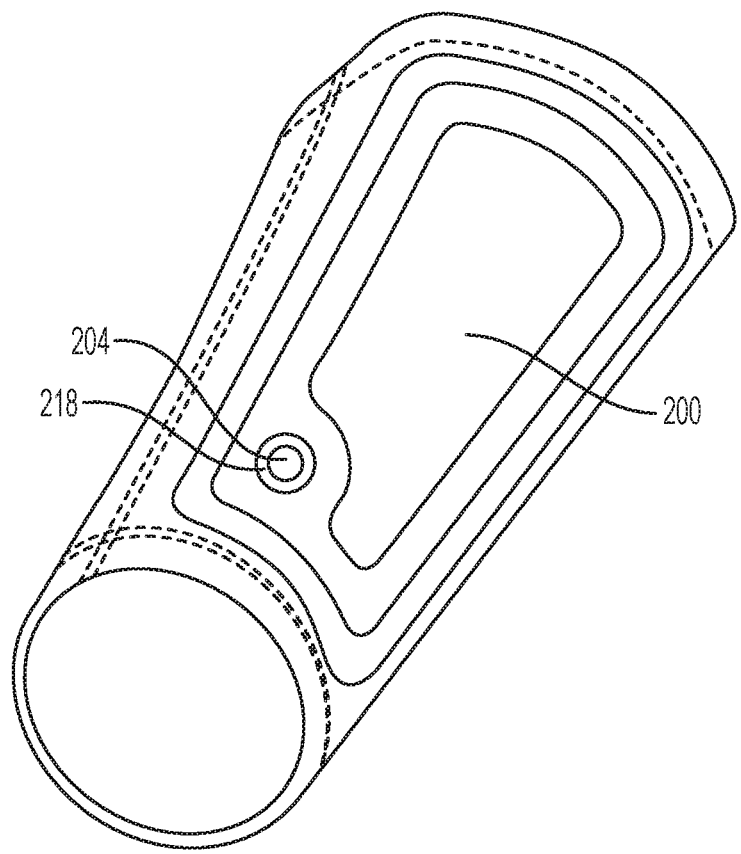
FIG. 18 is a close-up view of a hydration sleeve that can be integrated into a garment, according to an embodiment.
Figure 19:
FIG. 19 is a front-facing view of a garment having an integrated hydration sleeve, according to an embodiment.
Figure 20:
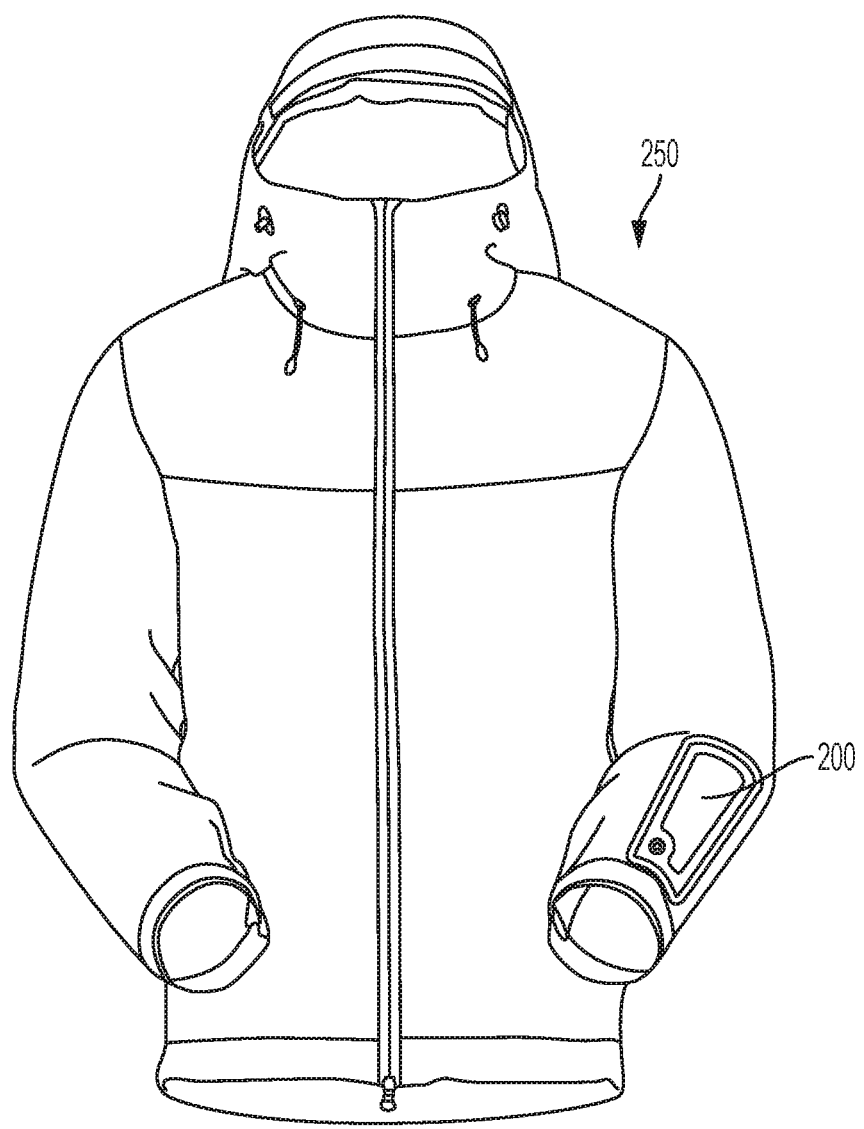
FIG. 20 is a front-facing view of a garment having an integrated hydration sleeve, according to an embodiment.

FIGS. 18-20 depict another embodiment of a hydration sleeve 200 integrated into the forearm of an outerwear garment 250. The hydration sleeve 200 of FIGS. 18-20 can be configured so as to be an integral component of the garment 150, which may negate the need for an adjustment strap. For example, according to an embodiment, the hydration sleeve 200 may comprise one or more layers of fabric that overlay the outer fabric layer of the garment, to form a pocket for receipt of a hydration bladder. As with other embodiments, the hydration sleeve 200 can include a port 218 for passage of the hydration bladder mouthpiece 204 therethrough. FIG. 19 shows the hydration sleeve built into the forearm of an outerwear garment 250, in this case a long-sleeve athletic shirt. Edges of the hydration sleeve 200 fabric can be attached, for example sewn or bonded, directly to the fabric of the outerwear garment 250. FIG. 18 depicts an embodiment of a pre-formed hydration sleeve construction that incorporated as part of a garment sleeve, for example, during manufacture, to provide a garment having an integrated hydration sleeve. FIG. 18 also shows that the hydration sleeve 200 can have a mouthpiece port 218 in a distal position of the hydration sleeve 200.

FIG. 20 shows the hydration sleeve 200 built into the forearm of another outerwear garment 250, in this case a coat. In the embodiments of FIGS. 19 and 20, the garment can include a bladder pocket that receives the hydration bladder. According to embodiments, the hydration sleeve 200 can be configured with an insulated layer to insulate the user from hot or cold temperatures caused by the contents of the hydration bladder. According to embodiments, the insulating layer can be disposed in between the user and the interior wall of the hydration sleeve 200 and/or garment. For extreme conditions, the hydration sleeve 200 can be configured with an additional insulating layer in between the contents of the hydration sleeve and the exterior wall of the hydration sleeve to minimize the likelihood that the contents of the hydration sleeve 200 become frozen.

FIGS. 19 and 20 show that the hydration sleeve 200 can be attached at the forearm of the garments. However, other embodiments are contemplated within the broad inventive principles disclosed herein. For example, the hydration sleeve 200 can be located in positions on the outerwear garment on the upper arm, the shoulder, the chest, the back, etc. FIG. 19 shows that the hydration sleeve 200 is configured on the left sleeve of the user's outerwear garment 250. The hydration sleeve 200 can be disposed on either sleeve, and can be adapted on the dominant arm of the user or on the non-dominant arm of the user.

Accordingly, a portion of the hydration sleeve (e.g., formed from either spandex, Lycra™, Elastane, polyester, elastic, polyurethane, neoprene, polypropylene, other known "stretchy" fabrics used in athletic gear, or combinations thereof) can either be interposed beneath, or embedded within a layer of an outerwear garment. According to embodiments with the adjustable strap, the adjustable strap including the bladder pocket frame and mouthpiece can be securely attached to the exterior of the outerwear garment, for example, by stitching, bonding, or adhesives. The outerwear garment can also encompass an additional opaque flap large enough to cover a portion of, or the entire hydration sleeve with adjustable strap. One end of the flap can encompass a Velcro™, zipper, snap or other known fastener to securely link the flap with the base layer of the outerwear garment. The flap can also encompass a small hole roughly the same diameter of the mouthpiece that allows the user to access the mouthpiece. The outerwear garment type can include, but is not limited to, long-sleeved athletic shirts, sweatshirts, jackets, coats, or wetsuits. Embodiments of the hydration sleeve 200 used with, or incorporated into, a garment can utilize sensor technology as described above under the heading "Other Features," as will be appreciated by one of skill in the art based on this disclosure.

The embodiments illustrated and discussed in this specification are intended only to teach those skilled in the art the best way known to the inventors to make and use the invention. Nothing in this specification should be considered as limiting the scope of the present invention. All examples presented are representative and non-limiting. The above-described embodiments of the invention may be modified or varied, without departing from the invention, as appreciated by those skilled in the art in light of the above teachings. It is therefore to be understood that, within the scope of the claims and their equivalents, the invention may be practiced otherwise than as specifically described.

The invention claimed is:

1. A wearable hydration device, comprising:
   a tubular sleeve having an interior surface and an exterior surface;
   an outer layer surrounding the tubular sleeve, the outer layer including a strap, a bladder pocket formed in the outer layer, and a bladder pocket opening;
   wherein the bladder pocket is configured to receive a hydration bladder through the bladder pocket opening; and
   wherein the strap is configured to extend over the exterior surface of the tubular sleeve between a first side of the bladder pocket and a second side of the bladder pocket.

2. The device of claim 1, wherein the bladder pocket defines a mouthpiece port.

3. The device of claim 1, the strap further comprising a first portion and a second portion, wherein one of the first and second portions includes a fastener and another of the first and second portions includes a loop that is configured to receive the fastener.

4. The device of claim 1, further comprising:
   at least one cuff disposed distally and/or proximally to the sleeve.

5. The device of claim 1, further comprising:
   an insulation layer between the sleeve and the bladder pocket.

6. The device of claim 1, wherein the bladder pocket includes a non-stretch bladder pocket frame and includes at least one stretch panel.

7. The device of claim 1, wherein the strap includes a first portion including a hook portion of a hook and loop fastener, and the strap includes a second portion including a loop portion of the hook and loop fastener.

8. The wearable hydration device of claim 1, wherein the bladder pocket is secured to the outer layer around a perimeter of the bladder pocket and wherein the bladder pocket opening extends through the bladder pocket.

9. A hydration system, comprising:
a garment having an exterior face;
a hydration sleeve integrated into a forearm portion of the garment, the hydration sleeve comprising a layer of sleeve material overlaying the garment exterior face, the layer of sleeve material defining a bladder pocket configured to receive a hydration bladder;
an insulated layer disposed between a user and an interior wall of the hydration sleeve, the exterior face of the garment, or both the interior wall of the hydration sleeve and the exterior face of the garment; and
a mouthpiece port extending through the layer of sleeve material.

10. The hydration system of claim 9, further comprising a mouthpiece within the mouthpiece port, the mouthpiece adjacent the mouthpiece port.

11. A pre-filled, single-use hydration bladder, comprising:
a sealed pouch having an interior chamber pre-filled with at least one of a liquid and an energy gel; and
a port that is-configured to receive a mouthpiece, the port providing fluid communication between the interior chamber and outside of the pouch, wherein the hydration bladder is shaped to fit inside a bladder pocket that is fixed to a user,
wherein the port includes a fitment located on a face of the sealed pouch and affixed to the sealed pouch, the fitment configured to enable a connection between the bladder and a mouthpiece, wherein the fitment includes a frangible seal that seals the hydration bladder.

12. The bladder of claim 11, further comprising a mouthpiece attached to the port.

* * * * *